(12) United States Patent
Kim et al.

(10) Patent No.: US 9,874,500 B2
(45) Date of Patent: Jan. 23, 2018

(54) CARTRIDGE-TYPE APPARATUS FOR FIXING BIOLOGICAL SAMPLE USING MICROWAVES

(71) Applicant: Medicson Co., Ltd., Asan-si, Chungcheongnamdo (KR)

(72) Inventors: Young In Kim, Anyang-si (KR); Chang Wan Jeon, Seoul (KR)

(73) Assignee: Medicson Co., Ltd., Asan-si, Chungcheongnamdo (KR)

( * ) Notice: Subject to any disclaimer, the term of this patent is extended or adjusted under 35 U.S.C. 154(b) by 0 days.

(21) Appl. No.: 15/348,991

(22) Filed: Nov. 11, 2016

(65) Prior Publication Data

US 2017/0199105 A1    Jul. 13, 2017

(51) Int. Cl.
*G01N 1/31* (2006.01)
*G01N 33/48* (2006.01)

(52) U.S. Cl.
CPC ............... *G01N 1/31* (2013.01); *G01N 33/48* (2013.01)

(58) Field of Classification Search
CPC ............ G01N 1/30; G01N 1/31; G01N 1/312; G01N 1/36; G01N 1/44; G01N 1/06; G01N 1/00; G01N 33/48; G01N 33/54366; G01N 5/045; G01N 22/04; B01L 9/50; B01L 3/502; B01L 3/5021; H05B 6/806; H05B 6/70; H05B 6/80
USPC ....... 219/679, 736, 754, 755, 762, 678, 685, 219/687, 700, 745, 759; 435/40.5, 173.1, 435/173.4, 40.51, 40.52, 41, 6.11, 91.2
See application file for complete search history.

(56) References Cited

U.S. PATENT DOCUMENTS

| | | | | |
|---|---|---|---|---|
| 4,092,512 A * | 5/1978 | Suzuki | ................. | H02K 49/108 219/754 |
| 4,210,794 A * | 7/1980 | Oguri | ................... | H05B 6/6411 126/41 A |
| 4,330,696 A * | 5/1982 | Pomeroy | ............... | A47J 37/046 108/139 |
| 4,681,996 A * | 7/1987 | Collins | .................. | G01N 22/04 219/679 |
| 5,068,086 A * | 11/1991 | Sklenak | .................... | A01N 1/00 219/745 |
| 5,356,100 A * | 10/1994 | Bookwalter | ......... | A61G 13/101 248/122.1 |
| 5,499,872 A * | 3/1996 | Baxter | ................ | B01F 11/0014 366/208 |
| 6,077,788 A * | 6/2000 | Kawasaki | ................. | C23F 4/00 438/706 |
| 6,586,713 B2 * | 7/2003 | Essenfeld | ................. | B01L 9/50 219/679 |

(Continued)

FOREIGN PATENT DOCUMENTS

KR     10-1242603 B1     3/2013
KR     20-2013-0004266 U     7/2013

*Primary Examiner* — David A Vanore
(74) *Attorney, Agent, or Firm* — Revolution IP, PLLC

(57) ABSTRACT

Disclosed is a cartridge-type apparatus for fixing a biological sample using microwaves. Particularly, the cartridge-type apparatus for fixing a biological sample using microwaves includes a resonance part having a cavity, a module for generating and amplifying microwaves configured to generate microwaves in the cavity, a cartridge which is disposed to be rotatable in the cavity and in which at least one wide-mouth bottle is placed, and a motor rotating the cartridge.

9 Claims, 6 Drawing Sheets

(56) References Cited

U.S. PATENT DOCUMENTS

| | | | | |
|---|---|---|---|---|
| 6,797,928 B2* | 9/2004 | Giberson | ............... | H05B 6/806 |
| | | | | 219/679 |
| 7,075,045 B2* | 7/2006 | Visinoni | ................. | G01N 1/30 |
| | | | | 219/685 |
| 8,831,776 B2* | 9/2014 | Lefebvre | ................. | G01N 1/36 |
| | | | | 435/40.5 |
| 9,217,696 B2* | 12/2015 | Morales | ................. | G01N 1/06 |
| 9,600,876 B2* | 3/2017 | Whited | ................. | G06T 7/0012 |
| 2001/0051365 A1* | 12/2001 | Morales | ................. | B01L 9/50 |
| | | | | 435/173.4 |
| 2008/0233590 A1* | 9/2008 | Ronacher | ............ | B01F 7/00816 |
| | | | | 435/6.11 |
| 2017/0199105 A1* | 7/2017 | Kim | ...................... | G01N 33/48 |

* cited by examiner

CARTRIDGE-TYPE APPARATUS FOR FIXING BIOLOGICAL SAMPLE USING MICROWAVES

CROSS-REFERENCE TO RELATED APPLICATION

This application claims priority to and the benefit of Korean Patent Application No. 2016-0003308, filed on Jan. 11, 2016, the disclosure of which is incorporated herein by reference in its entirety.

BACKGROUND OF THE INVENTION

1. Field of the Invention

The present disclosure relates to a cartridge-type apparatus for fixing a biological sample using microwaves.

2. Description of the Related Art

Tissues for diagnosing a tumor (hereinafter referred to as a biological sample) are subjected to microscopic examination. Here, a chemical fixing agent is generally used to fix a biological sample.

Fixing a biological sample through chemical fixation takes 24 hours or more, and even if the fixation is performed under ideal conditions, alterations of hyperfine structures, i.e., elution and conformational changes of proteins, lipids, etc., may occur. To overcome these limitations, a rapid fixation method using microwaves, such as a method using a rapid tissue processor, has been used.

Conventional technology using a rapid fixation method uses a device having a structure composed of a microwave oven equipped with a magnetron. A schale containing a biological sample, a saline solution, and formalin or alcohol is inserted into the microwave oven of the device, and then the biological sample is subjected to fixation. However, when a plurality of schales are inserted into the microwave oven, the plurality of schales cannot be uniformly irradiated by microwaves, and thus microwave energy absorbed by each shale may be different.

SUMMARY OF THE INVENTION

Therefore, the present disclosure has been made in view of the above problems, and it is an objective of the present disclosure to provide a cartridge-type apparatus for fixing a biological sample using microwaves that uniformly irradiates a plurality of wide-mouth bottles containing biological samples with microwaves and simultaneously processes the wide-mouth bottles.

In accordance with the present disclosure, the above and other objects can be accomplished by the provision of a cartridge-type apparatus for fixing a biological sample using microwaves comprising: a resonance part having a cavity; a module for generating and amplifying microwaves configured to generate microwaves in the cavity; a cartridge which is disposed to be rotatable in the cavity and in which at least one wide-mouth bottle is placed; and a motor rotating the cartridge.

The module for generating and amplifying microwaves may include a microwave generator; and a mode excitor which is disposed at the resonance part and connected to the microwave generator and from which microwaves are output.

The cartridge-type apparatus may further include a matching stub that is disposed at the cavity and matches the microwave frequency radiated from the mode excitor to the resonance part.

The resonance part may include a body, an upper surface of which is open and an interior of which thus has a cavity, a door that is disposed at an upper surface of the body; and a sensor that is disposed at the body and senses opening and closing of the door, wherein, when the sensor senses opening of the door, the module for generating and amplifying microwaves and the motor do not operate.

The resonance part may further include a locking part that is disposed at the body and maintains a closed state of the door.

The cartridge-type apparatus may further include a housing, at an empty interior of which the resonance part is disposed, wherein an upper surface of the housing is open and the open upper surface of the housing is connected to the door.

The cartridge-type apparatus may further include a shaft that connects the motor to the cartridge.

The cartridge may include a center member that is connected to the shaft; and a member for fixing wide-mouth bottles that is formed along a circumference of the center member and has positioning grooves in which the wide-mouth bottles are placed, wherein the shaft penetrates a center of the center member, and a part at which the shaft faces the center member is formed as a flat surface.

The cartridge-type apparatus may further include a support which divides the cavity and thus divides the cavity into a space for the cartridge and space for the module for generating and amplifying microwaves and through which the shaft penetrates.

A driving shaft of the motor may be inserted into the shaft and at least a portion of a part at which the driving shaft and the shaft face may have a flat surface.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE INVENTION

Figure 1:
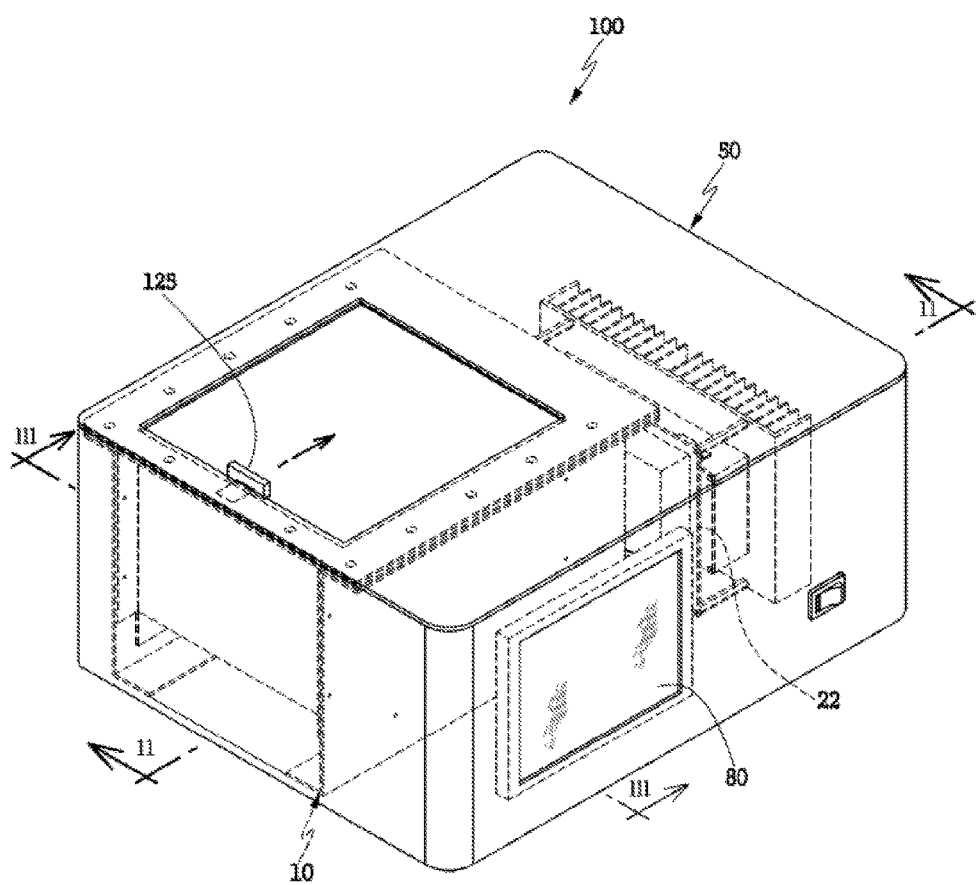
FIG. 1 illustrates a perspective view of a cartridge-type apparatus for fixing a biological sample using microwaves according to an embodiment of the present disclosure.

Exemplary embodiments of the present invention are described in detail so that it can be easily implemented by those of ordinary skill in the art with reference to the accompanying drawings. However, the present invention may be implemented in various different forms and is not limited to these embodiments. To clearly describe the present invention, parts not related to the description are omitted in the drawings, and like reference numerals in the specification denote like elements.

Hereinafter, a cartridge-type microwave biological sample fixing apparatus according to an embodiment of the present disclosure will be described with reference to FIGS. 1 to 6.

Figure 2:
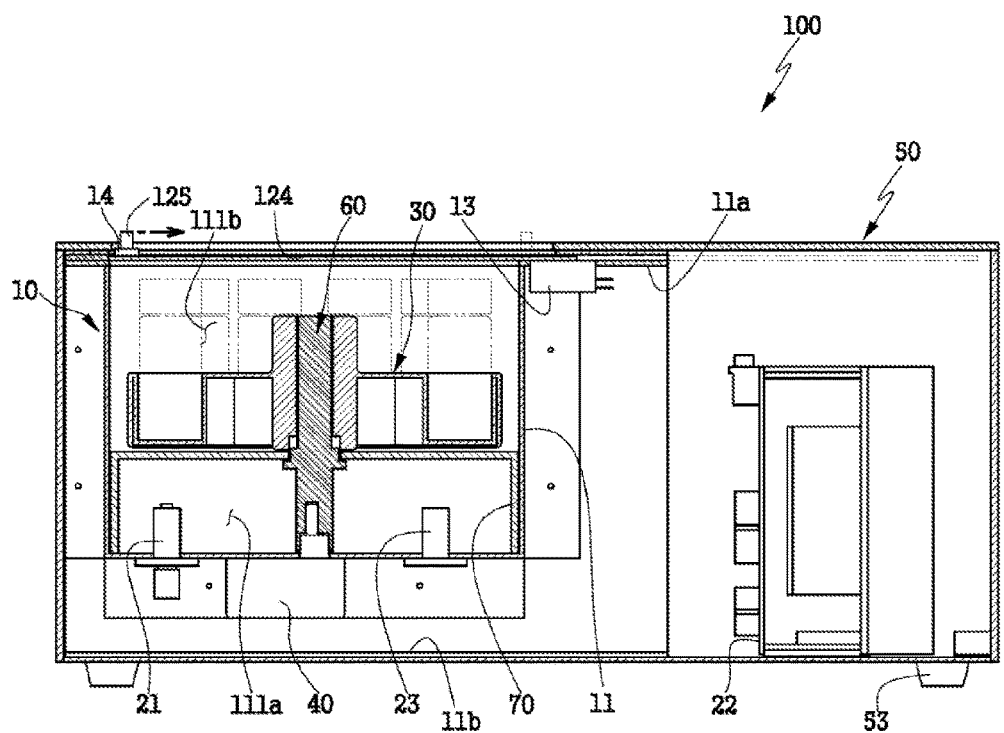
FIG. 2 illustrates a sectional view taken along line II-II of FIG. 1.
Figure 3:
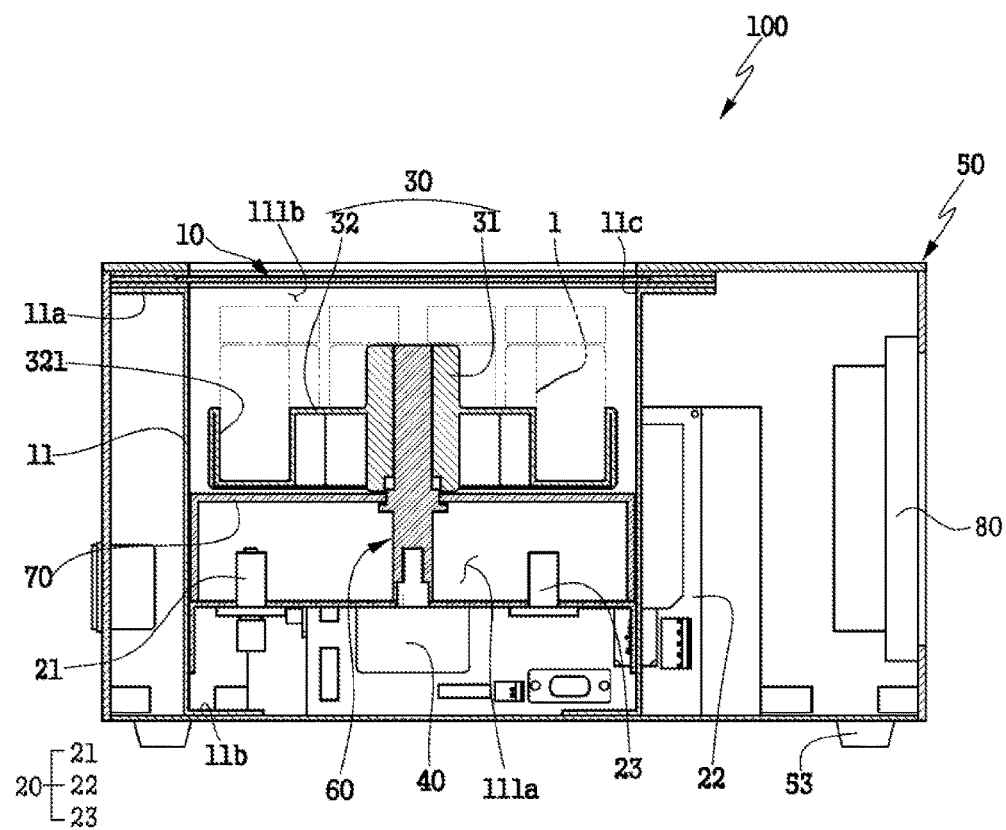
FIG. 3 illustrates a sectional view taken along line of FIG. 1.
Figure 4:
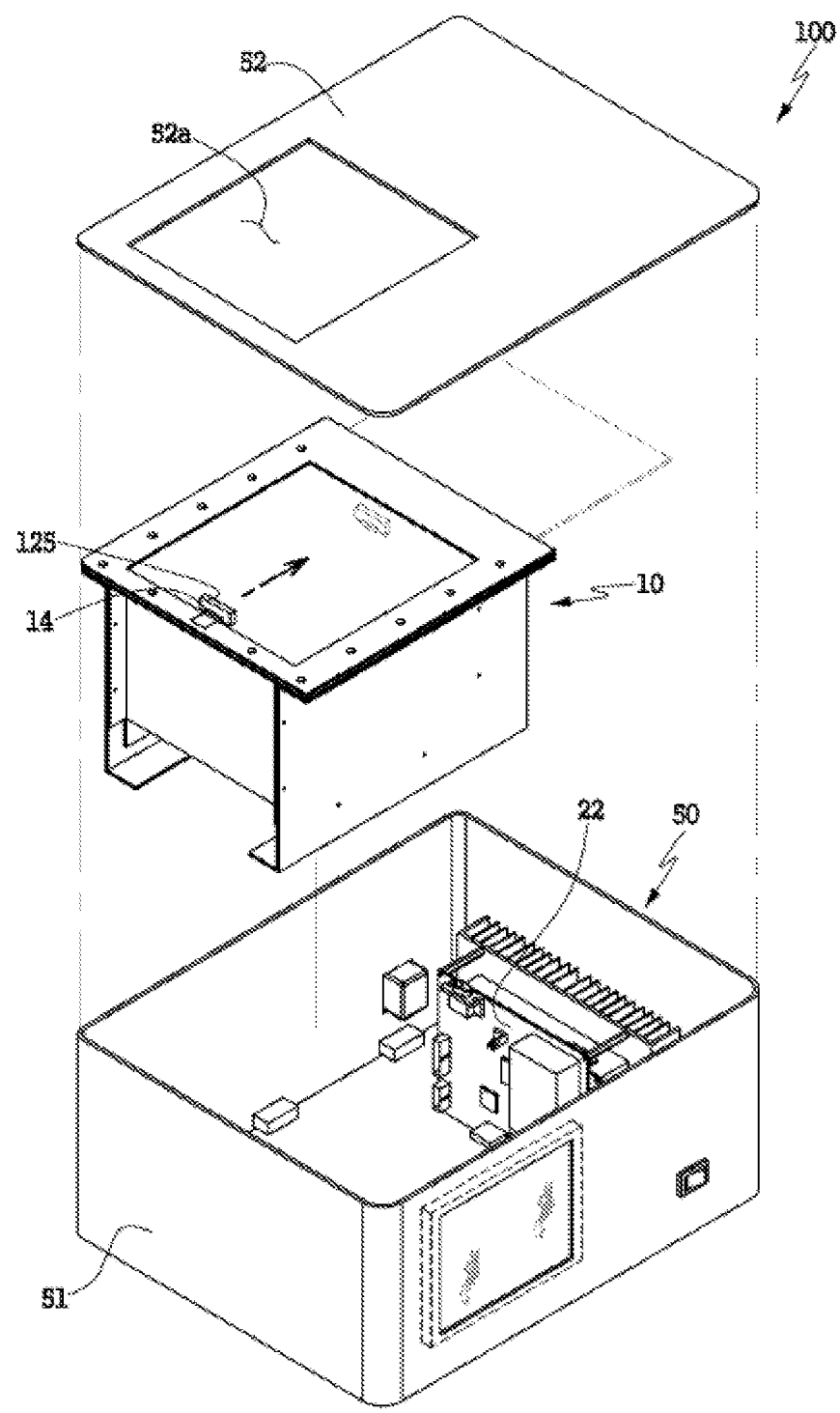
FIG. 4 illustrates an exploded perspective view of FIG. 1.
Figure 5:
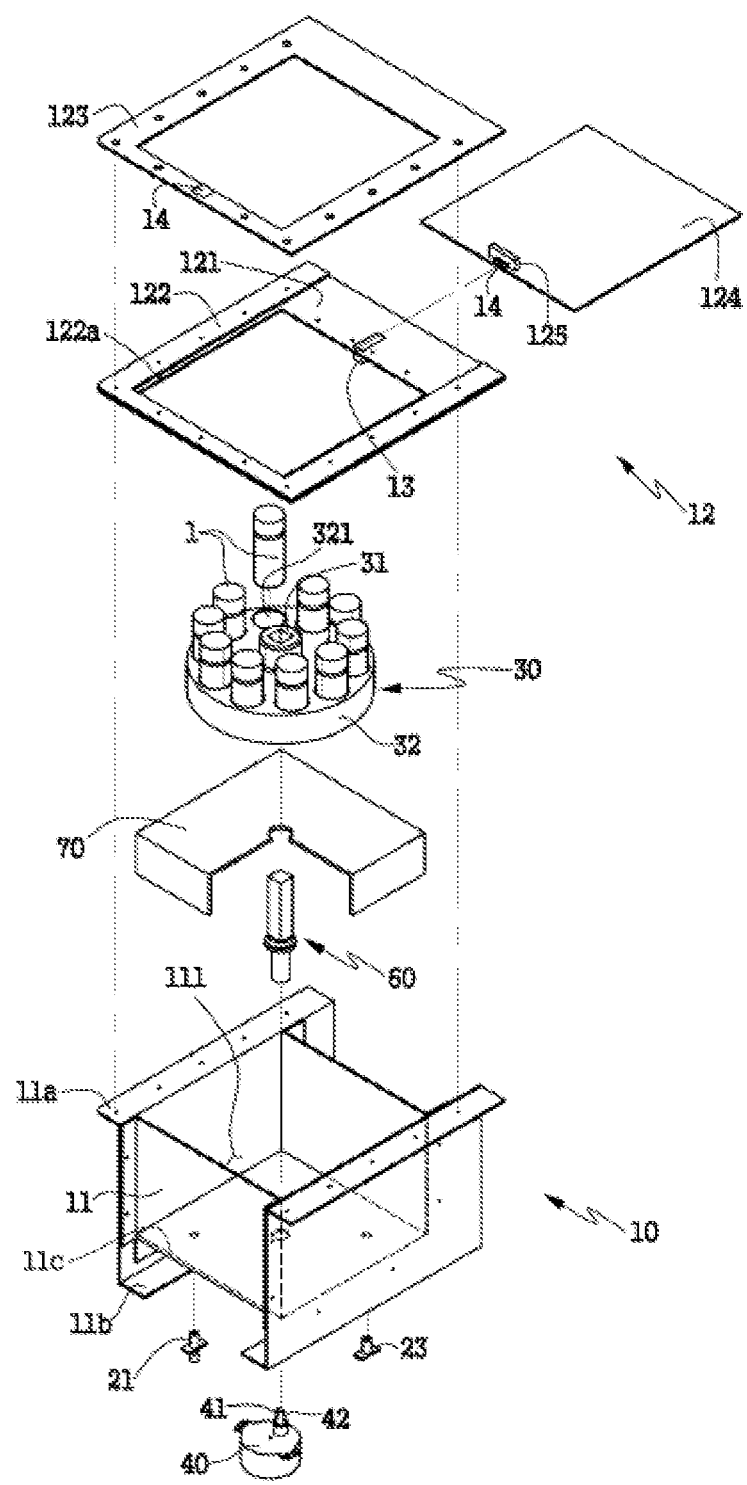
FIG. 5 illustrates an exploded perspective view of a cartridge and resonance part of FIG. 2.
Figure 6:
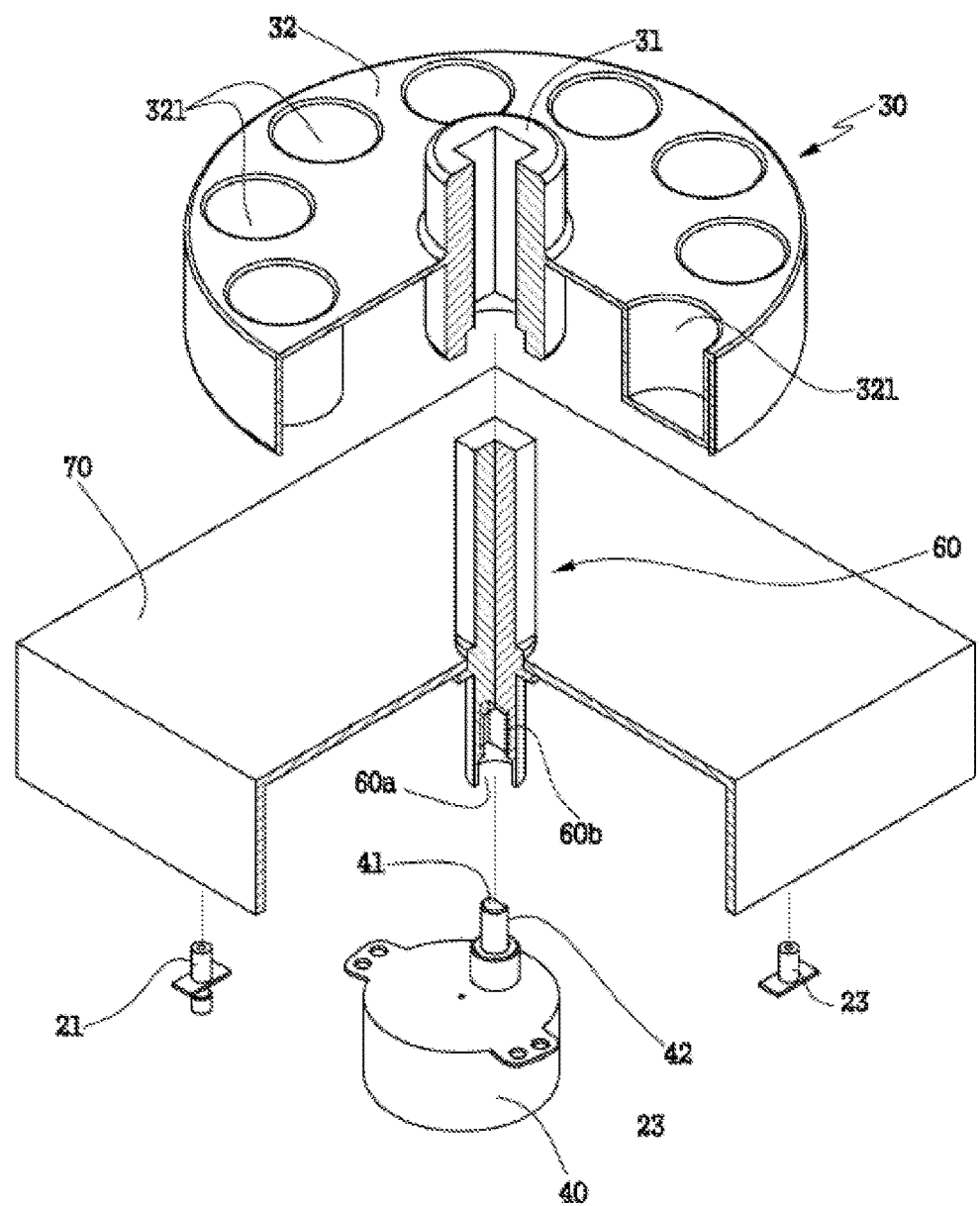
FIG. 6 illustrates an exploded perspective view of a cartridge and body of FIG. 5.

FIG. 1 illustrates a perspective view of a cartridge-type apparatus for fixing a biological sample using microwaves according to an embodiment of the present disclosure, FIG. 2 illustrates a sectional view taken along line II-II of FIG. 1, FIG. 3 illustrates a sectional view taken along line of FIG. 1, FIG. 4 illustrates an exploded perspective view of FIG. 1, FIG. 5 illustrates an exploded perspective view of a cartridge and resonance part of FIG. 2, and FIG. 6 illustrates an exploded perspective view of a cartridge and body of FIG. 5.

Referring to FIGS. 1 to 6, a cartridge-type apparatus for fixing a biological sample using microwaves 100 according to an embodiment of the present disclosure includes a housing 50, a resonance part 10, a support 70, a motor 40, a shaft 60, a cartridge 30, a module 20 for generating and amplifying microwaves, and a matching stub 23.

The housing 50 includes a main body 51 and a cover 52 and forms the exterior of the cartridge-type apparatus for fixing a biological sample using microwaves 100.

An interior of the main body 51 is empty and an upper surface of the main body 51 is open. The interior of the main body 51 has a space in which the resonance part 10, the module 20 for generating and amplifying microwaves, the matching stub 23, the cartridge 30, the motor 40, the shaft 60, and the support 70 are disposed. A pad 53 for preventing slippage of the main body 51 is attached to a lower surface of the main body 51.

At least a portion of a front surface of the main body 51 is open and a touch panel 80 is disposed at the open portion of the main body 51. Data may be input to control the module 20 for generating and amplifying microwaves, the motor 40, and the like by means of the touch panel 80. Meanwhile, data (temperature, fixation time, etc.) may be displayed on the touch panel 80.

The cover 52 is disposed to be separated from the upper part of the main body 51. At least a portion of the cover 52 is open (52a).

In accordance with a design of the housing 50, the cover 52 may be equipped with the touch panel 80. A data display means is not limited to the touch panel 80 and may have a switch structure.

The resonance part 10 includes a body 11, a door 12, a sensor 13, and a locking part 14, and an electromagnetic field having a natural frequency is present in the resonance part 10. The resonance part 10 may be made of a metal.

The body 11 has a cavity 111 in an interior thereof and an upper surface of the body 11 is open (11c). The opening 11c is connected to the opening 52a. A lower surface of the body 11 is spaced apart from an interior bottom of the main body 51, and a circumference of the body 11 is spaced apart from an interior circumference of the main body 51. Lower parts 11b of front and rear surfaces of the body 11 extend to an interior bottom of the body 11 and thus are fixed to the interior bottom of the main body 51. The body 11 is fixed to the main body 51 by rivets, welding, etc. Upper parts 11a of the front and rear surfaces of the body 11 are bent toward the interior of the main body 51.

A door 124 is disposed between an upper part 11a of the body 11 and the cover 52, includes first, second, and third plates 121, 122, and 123 and the sliding door 124, and opens and closes the openings 11c and 52a.

The upper part 11a and the first, second, and third plates 121, 122, and 123 are sequentially stacked in this order and fixed to each other with screws. However, a coupling means among the upper part 11a, the first, second, and third plates 121, 122, and 123 is not limited to screws.

Upper and lower parts of portions that correspond to the openings 11c and 52a, of the first, second, and third plates 121, 122, and 123 are penetrated. The second plate 122 is upwardly and downwardly penetrated and opens to the right.

The first plate 121 is coupled with an upper surface of the upper part 11a. The second plate 122 is disposed on the first plate 121 and the third plate 123 is disposed on the second plate 122. An upper surface of the third plate 123 faces a lower surface of the cover 52. The second plate 122 is disposed between the first plate 121 and the third plate 123 to form a groove for sliding 122a.

The door 124 has predetermined dimensions and is located at a position of the openings 11c and 52a. An edge of the door 124 is inserted into the groove for sliding 122a. The door 124 moves along the groove for sliding 122a through the open right side of the second plate 122 and thus may open and close the openings 11c and 52a.

A knob 125, which a user may hold, is disposed at a left side of the door 124.

The locking part 14 is disposed at the door 124 such that, when the openings 11c and 52a are closed by the door 124, the closed state of the door 124 is maintained. The locking part 14 may be disposed at the second plate 122. The locking part 14 is constituted of a permanent magnet. Accordingly, a portion of the first plate 121 or a portion of the door 124 which contacts the locking part 14 may be made of a magnetic sub stance.

The door 124, which is described as having a sliding structure in the accompanying drawings and the aforementioned description, is connected to the body 11 by a hinge.

The sensor 13 is disposed at the door 12 and senses opening and closing of the door 124. When the sensor 13 senses closing of the door 124, the motor 40 and the module 20 for generating and amplifying microwaves may operate. On the other hand, when the sensor 13 senses opening of the door 124, operation of the motor 40 and the module 20 for generating and amplifying microwaves may be stopped.

Meanwhile, although the door 124 has been described as being fixed by the first, second, and third plates 121, 122, and 123, the first, second, and third plates 121, 122, and 123 may be omitted and the door 124 may be coupled with the cover 52 to open and close the openings 11c and 52a.

The support 70 is disposed at and thus divides the cavity 111. By the support 70, the cavity 111 is divided into a cartridge area 111b at which the cartridge 30 is located and a microwave generation area 111a at which a mode excitor 21 and the matching stub 23 of the module for generating and amplifying microwaves 20 are located. The support 70 may be made of a non-conductor such as plastic.

The motor 40 is coupled with a lower surface of the body 11. A driving shaft 41 of the motor 40 penetrates the lower surface of the body 11 and is thus located at the microwave generation area 111a. At least a portion of the driving shaft 41 has a flat surface 42 in upper and lower directions. The motor 40 generates torque to rotate the cartridge 30. The motor 40 may operate only when the door 124 is closed.

The shaft 60 has a predetermined length and penetrates the support 70. An upper part of the shaft 60 is located at the outside of the microwave generation area 111a and a lower part of the shaft 60 is located at the microwave generation area 111a. An outer surface of the upper part of the shaft 60 is formed of a flat surface 60b in a length direction.

At the lower part of the shaft 60, an insertion groove 60a into which the driving shaft 41 is inserted is formed. At an interior of the shaft 60, the flat surface 60b facing the flat surface 42 is formed. Due to coupling of the flat surface 42 with the flat surface 60b, the shaft 60 may rotate along the driving shaft 41 when the driving shaft 41 rotates.

As illustrated in FIG. 6, the cartridge 30 includes a center member 31 and a member for fixing wide-mouth bottles 32 and is located at the cartridge area 111b. One or more wide-mouth bottles 1 containing biological samples may be placed in the cartridge 30. The cartridge 30 may be made of the same material as the support 70.

The center member 31 has a predetermined length and is spaced apart from an upper part of the support 70. A lower surface of the center member 31 is spaced apart from the upper surface of the support 70. An upper part of the shaft 60 is inserted into an interior center of the center member 31. An interior shape of the center member 31 into which the shaft 60 is inserted is the same as a shape of the shaft 60.

The member for fixing wide-mouth bottles 32 is cylindrical, and the center member 31 is located at a center of the member for fixing wide-mouth bottles 32. That is, the member for fixing wide-mouth bottles 32 is formed along an exterior circumference of the center member 31. A lower surface of the member for fixing wide-mouth bottles 32 is spaced apart from the upper surface of support 70. The member for fixing wide-mouth bottles 32 includes positioning grooves 321 that are dented toward the upper surface of the support 70. The positioning grooves 321 are formed along a circumference of the member for fixing wide-mouth bottles 32 while spaced from each other. At least portion of a wide-mouth bottle 1 is inserted into the positioning grooves 321 and thus the wide-mouth bottle 1 may be fixed. The number of positioning grooves 321 may be varied according to a design of the cartridge 30.

Torque of the shaft 60 is transmitted to the center member 31 and thus the cartridge 30 may rotate. The cartridge 30 is rotated in a state in which the openings 11c and 52a are closed by the door 124.

The module for generating and amplifying microwaves 20 includes the mode excitor 21 and the microwave generator 22. The microwave generator 22 may include a microprocessor, a memory, an amplifier, etc.

The mode excitor 21 and the matching stub 23 are disposed at the microwave generation area 111a and fixed to a bottom of the body 11. The microwave generator 22 is constituted of a circuit and is fixed to an interior circumference of the main body 51. The mode excitor 21, the touch panel 80, a display part 90, etc. are electrically connected to the microwave generator 22.

Description of a particular constitution of the module 20 for generating and amplifying microwaves is omitted because constitutions of generally known microwave generators may be adopted for the module 20 for generating and amplifying microwaves.

Microwaves generated by the microwave generator 22 are radiated to the cavity 111 through the mode excitor 21. The radiated microwaves have a frequency domain of 2.45 GHz. The microwave generator 22 includes a microprocessor, a memory, an interface for controlling input and output, a power supply part, etc. When a signal of radiated microwaves is weak, the microwave generator 22 may amplify the signal to a sufficient magnitude to fix a biological sample.

Meanwhile, the microwave generator 22 may be connected to an external device (not shown). The external device may display or control a state of the cartridge-type apparatus for fixing a biological sample using microwaves 100 and may be a computer, a mobile phone, or the like.

The matching stub 23 has a predetermined volume, is located at the cavity 111, and reduces dimensions of the cavity 111. A frequency of a signal of microwaves radiated to the cavity 111 may be decreased by the cartridge 30, the wide-mouth bottles 1, biological samples, a solution, etc., and thus it may not maintain 2.45 GHz. Accordingly, the matching stub 23 has an effect of reducing the dimensions of the cavity 111. The matching stub 23 matches the radiated microwave frequency to 2.45 GHz. The microwave frequency may be varied depending upon biological samples, a structure of a resonance part, etc.

Meanwhile, the wide-mouth bottles 1 may pass over the mode excitor 21 due to rotation of the cartridge 30. Accordingly, microwaves may be equally applied to the wide-mouth bottles 1.

In the aforementioned description and the accompanying drawings, the wide-mouth bottles 1 were described as being placed in the positioning grooves 321. However, instead of the wide-mouth bottles 1, schales may be applied. Here, the structure of the positioning grooves 321 may be changed according to the structure of the schales.

Hereinafter, functions of the cartridge-type apparatus for fixing a biological sample using microwaves 100 will be described referring to FIGS. 1 to 6.

An irradiation time of microwaves is set depending upon the types and sizes of biological samples. That is, the microwave irradiation time is set differently according to biological sample types.

A biological sample to be fixed is fed into the wide-mouth bottle 1, and then a saline solution, formalin, or alcohol is fed into the wide-mouth bottle 1 such that the biological sample is not exposed to the air. In a state in which the door 124 is open, a lower part of the wide-mouth bottle 1 is inserted into one of the positioning grooves 321 and then fixed. Here, the wide-mouth bottle 1 may be inserted into each of the positioning grooves 321 and fixed therein. The door 124 is closed. The closed state of the door 124 is stably maintained by the locking part 14.

When the closing of the door 124 is sensed by the sensor 13, the microwave generator 22 drives the motor 40 and causes the mode excitor 21 to radiate microwaves.

Energy of the radiated microwaves may be applied to the biological sample in the wide-mouth bottle 1. Water molecules in the wide-mouth bottle 1 collide with each other due to the microwaves. Accordingly, heat is applied to the biological sample, whereby the biological sample is fixed.

Meanwhile, the microwave generator 22 senses heat applied to the biological sample, and when the sensed temperature reaches a set temperature, the mode excitor 21 may stop. When the door 124 is open, the motor 40 and the microwave generator 22 are stopped due to sensing of the sensor 13. Accordingly, microwaves are not radiated by the mode excitor 21 and rotation of the cartridge 30 is stopped.

In addition, data on the fixation of the biological sample data (e.g., data on irradiation time, irradiation temperature, etc.) is transmitted to an exterior device via an interface of the microwave generator 22.

When operation of each of the components is completed, the wide-mouth bottle 1 containing the fixed biological sample is taken out of the positioning grooves 321.

According to an embodiment of the present disclosure, a cartridge in which a plurality of wide-mouth bottles may be disposed is disposed at a cavity and the cartridge may be rotated by the cavity. Due to rotation of the cartridge, each of the wide-mouth bottles may be uniformly irradiated with microwaves. Accordingly, a plurality of biological samples may be simultaneously processed, whereby a time used to fix biological samples may be minimized.

According to an embodiment of the present disclosure, since microwaves are applied to the biological samples contained in the wide-mouth bottles, a fixation time of the biological samples is short and cytoplasmic degeneration does not occur. In addition, superior stainability may be provided. In particular, antigen shielding and antigenicity loss do not occur.

Although preferred embodiments of the present disclosure have been described in detail above, the embodiments are provided for illustrative purposes only and should not be construed as limiting the scope and spirit of the present disclosure. It will be understood by those of ordinary skill in the art that various changes in form and details may be made therein without departing from the spirit and scope of the present invention as defined by the following claims.

What is claimed is:

1. An apparatus for fixing a biological sample using microwaves comprising:
    a resonance part having a cavity;
    a module for generating and amplifying microwaves configured to generate microwaves in the cavity;
    a cartridge which is disposed to be rotatable in the cavity and in which at least one wide-mouth bottle is placed;
    a motor rotating the cartridge, and
    a shaft connecting the motor to the cartridge.

2. The apparatus according to claim 1, wherein the module for generating and amplifying microwaves comprises:
    a microwave generator; and
    a mode excitor which is disposed at the resonance part and connected to the microwave generator and from which microwaves are output.

3. The apparatus according to claim 2, further comprising a matching stub that is disposed at the cavity and matches the microwave frequency radiated from the mode excitor to the resonance part.

4. The apparatus according to claim 1, wherein the resonance part comprises:
    a body, an upper surface of which is open and thus an interior of which has a cavity,
    a door that is disposed at an upper surface of the body; and
    a sensor that is disposed at the body and senses opening and closing of the door,
    wherein, when the sensor senses opening of the door, the module for generating and amplifying microwaves and the motor do not operate.

5. The apparatus according to claim 4, wherein the resonance part further comprises a locking part that is disposed at the body and maintains a closed state of the door.

6. The apparatus according to claim 4, further comprising a housing, at an empty interior of which the resonance part is disposed, wherein an upper surface of the housing is open and the open upper surface of the housing is connected to the door.

7. The apparatus according to claim 1, wherein the cartridge comprises:
    a center member that is connected to the shaft; and
    a member for fixing wide-mouth bottles that is formed along a circumference of the center member and has positioning grooves in which the wide-mouth bottles are placed,
    wherein the shaft penetrates a center of the center member, and a part at which the shaft faces the center member is formed as a flat surface.

8. The apparatus according to claim 1, further comprising a support which divides the cavity and thus divides the cavity into a space for the cartridge and space for the module for generating and amplifying microwaves and through which the shaft penetrates.

9. The apparatus according to claim 1, wherein a driving shaft of the motor is inserted into the shaft and at least a portion of a part at which the driving shaft and the shaft face has a flat surface.

* * * * *